US008765479B1

(12) United States Patent
Kulkarni (10) Patent No.: US 8,765,479 B1
(45) Date of Patent: Jul. 1, 2014

(54) METHODS FOR DETERMINING THE RISK OF CORONARY HEART DISEASE AND CLINICAL MANIFESTATIONS OF CORONARY HEART DISEASE

(75) Inventor: Krishnaji R. Kulkarni, Birmingham, AL (US)

(73) Assignee: Atherotech, Inc., Birmingham, AL (US)

( * ) Notice: Subject to any disclaimer, the term of this patent is extended or adjusted under 35 U.S.C. 154(b) by 0 days.

(21) Appl. No.: 13/419,141

(22) Filed: Mar. 13, 2012

Related U.S. Application Data

(60) Provisional application No. 61/452,154, filed on Mar. 13, 2011.

(51) Int. Cl.
*G01N 33/92* (2006.01)
*G01N 33/48* (2006.01)

(52) U.S. Cl.
USPC ............... 436/71; 436/63; 435/11; 435/29

(58) Field of Classification Search
USPC ............... 436/63, 71, 174, 177; 435/11, 29
See application file for complete search history.

(56) References Cited

U.S. PATENT DOCUMENTS

| 2003/0008373 | A1* | 1/2003 | Bartel et al. | 435/226 |
|---|---|---|---|---|
| 2010/0179066 | A1* | 7/2010 | Chapman et al. | 506/7 |
| 2011/0137131 | A1* | 6/2011 | Adourian et al. | 600/300 |
| 2013/0045217 | A1* | 2/2013 | Laaksonen et al. | 424/172.1 |
| 2013/0316377 | A1* | 11/2013 | Penn et al. | 435/7.92 |

OTHER PUBLICATIONS

Durrington et al. British Heart Journal, vol. 56, 1986, pp. 206-212.*
Zhao et al. International Journal of Cardiology, vol. 63, 1998, pp. 161-164.*
Sodre et al. Journal of Clinical Laboratory Analysis, vol. 20, 2006, pp. 113-117.*
Nowicka et al. Clinica Chimica Acta, vol. 306, 2001, pp. 43-49.*
Abbott, et al. "High Density Lipoprotein Cholesterol, Total Cholesterol Screening, and Myocardial Infarction" Arteriosclerosis 8: 207-211, May/Jun. 1988.
Jones, et al. "Dabetes & Vascular Disease Research" Abstracts from the 5th Annual World Congress on the IRS; 2007; 4: 266.
Shah "Targeting Endogenous apo A-1—a new approach for rasing HDL" Nature Reviews Cardiology; 8: 187-188; Apr. 2011.
Alagona "Beyond LDL Cholesterol: The Role of Elevated Triglycerides and Low HDL Cholesterol in Residual CVD Risk Remaining After Statin Therapy" Am J. Manag Care; 2009; 15: S65-S73.
Journal of the American Heart Association "Third Report of the National Cholesterol Education Program (NCEP) Expert Panel on Detection, Evaluation, and Treatment of High Blood Cholesterol in Adults (Adult Treatment Panel III) Final Report" Circulation, 2002; 106: 3143-3421.
Ericsson, et al. "Effect of Bezafibrate Treatment Over Five Years on Coronary Plaques Causing 20% to 50% Diameter Narrowing (The Bezafibrate Coronary Atherosclerosis Intervention Trial [BECAIT])" Am J Cariol 1997; 80: 1125-1129.
Elam, et al. "Effect of Niacin on Lipid and Lipoprotein Levels and Glycemic Control in Patients with Diabetes and Peripheral Arterial Disease The ADMIT Study: A Randomized Trial" JAMA, Sep. 13, 2000; vol. 284, No. 10; 1263-1270.
Barter, et al. "Effects of Torcetrapid in Patients at High Risk for Coronary Events" N Engl J Med 2007; 357: 2109-2122.
Franceschini, et al. "A-I Milano Apoprotein Decreased High Density Lipoprotein Cholesterol Levels with Significant Lipoprotein Modifications and Without Clinical Atherosclerosis in an Italian Family" J. Clin. Invest. 1980; 66: 892-900.
Rubins, et al. "Gemfibrozil for the Secondary Prevention of Coronary Heart Disease in Men with Low Levels of High-Density Lipoprotein Cholesterol" N Engl J Med 1999; 341: 410-418.
Gofman, et al. "Ischennic Heart Disease, Atherosclerosis, and Longevity" American Heart Association, Circulation 1966; 34: 679-697.
Huttunen, et al. "The Helsinki Heart Study: Central Findings and Clinical Implications" Annals of Medicine 23: 155-159; 1991.
Asztalos "High-density lipoprotein metabolism and progression of atherosclerosis: new insights from the HDL Atherosclerosis Treatment Study" Curr Opin Cardiol 19: 385-391, 2004.
Castelli, et al. "Incidence of Coronary Heart Disease and Lipoprotein Cholesterol Levels" JAMA 196; 256: 2835-2838, 1986.
Kulkarni, et al. "Quantification of cholesterol in all lipoprotein classes by the VAP-II method" J Lipid Res 1994; 35: 159-168.
Kulkarni "Cholesterol Profile Measurement by Vertical Auto Profile Method" Clin Lab Med 26 (2006) 787-802.
Arsenault, et al. "Lipid parameters for measuring risk of cardiovasular disease" Nat. Rev. Cardiol. 8, 197-206 (2011).
Kamanna, et al. "Mechanism of Action of Niacin on Lipoprotein Metabolism" Current Atherosclerosis Reports 2000; 2: 36-46.
Miller, et al. "Relation of angiographically defined coronary artery disease to plasma lipoprotein subfractions and apolipoproteins" British Medical Journal 1981; 282: 1741-1744.
Nhlbi "NIH stops clinical trial on combination cholesterol treatment" NIH News 2011, p. 1-3.
Lipid Study Group "Prevention of Cardiovascular Events and Death with Pravastatin in Patients with Coronary Heart Disease and a Broad Range of Initial Cholesterol Levels" The New England Journal of Medicine; vol. 339: 19: 1349-1357, 1998.
Shepherd, et al. "Prevention of Coronary Heart Disease with Pravastatin in Men with Hypercholesterolemia" The New England Journal of Medicine 1995; 33: 20; 1301-1307.
Pedersen, et al. "Randomised trial of cholesterol lowering in 4444 patients with coronary heart disease: the Scandinavian Simvastatin Survival Study (4S)" Lancet 1994; 344: 1383-1389.

(Continued)

Primary Examiner — Maureen Wallenhorst
(74) Attorney, Agent, or Firm — Thomas G. Peterson; Bradley Arant Boult Cummings LLP (57) ABSTRACT

The present disclosure provides methods to predict the risk of CHD and/or clinical manifestations of CHD in a subject. In one embodiment, the method involves measuring the levels or concentration of apo A1, a subclass of HDL, $HDL_3$, or a combination of the foregoing. The methods of the present disclosure are particularly useful when the subject has reached target levels of one or more lipoproteins, such as, but not limited to, LDL or HDL or subclass of the foregoing.

18 Claims, 9 Drawing Sheets

(56) References Cited

OTHER PUBLICATIONS

Bersot, et al. "Risk determination of dyslipidemia in populations characterized by low levels of high-density lipoprotein cholesterol" Am Heart J 2003; 146: 1052-1060.

Rhoads, et al. "Serum Lipoproteins and Coronary Heart Disease in a Population Study of Hawaii Japanese Men" N Engl J Med 294: 293-298, 1976.

Sacks, et al. "The Effect of Pravastatin on Coronary Events After Myocardial Infarction in Patients with Average Cholesterol Levels" N Engl J Med 1996; 335: 1001-1009.

Miller, et al. "The Tomso Heart-Study High-Density Lipoprotein and Coronary Heart-Disease: A Prospective Case-Control Study" The Lancet Ltd, 1977; 8019: 965-968.

Davidson, et al. "Clinical utility of iinflammatory markers and advanced lipoprotein testing: Advice from an expert panel of lipid specialists" Journal of Clinical Lipidology (2011) 5, 338-367.

Myers et al. "Apolipoproteins A-1 and B and Cardiovascular Disease Risk" Chapter 6; Recommendations for Apolipoproteins A-1 and B pp. 35-41.

Grundy et al. "National Cholesterol Education Program Adult Treatment Panel III Report" 2001 pp. 1-85.

Goff DC Jr., et al. "A Report of the American College of Cardiology/American Heart Association Task Force on Practice Guidelines" 2013 ACC/AHA Cardiovascular Risk Guideline; pp. 1-50.

Stone NJ, et al. "A Report of the American College of Cardiology/American Heart Association Task Force on Practice Guidelines" 2013 ACC/AHA Blood Cholesterol Guideline; pp. 1-358.

* cited by examiner

Baseline characteristics of study participants (N=2,414) stratified by apolipoprotein (apo) A1 tertiles.

| Characteristics | Tertile 1 (≤105.6 mg/dL) | Tertile 2 (105.7-120.0 mg/dL) | Tertile 3 (>120.0 mg/dL) |
|---|---|---|---|
| Age (years) | 62.3±12.7 | 62.5±12.6 | 63.1±12.4 |
| Sex (male)* | 73.6% | 69.9% | 53.1% |
| Hypertension | 60.3% | 58.3% | 57.9% |
| Hyperlipidemia* | 58.0% | 54.2% | 50.4% |
| Diabetes* | 21.5% | 22.5% | 17.0% |
| Family History of coronary artery disease | 44.0% | 42.2% | 42.4% |
| Smoking | 17.3% | 18.2% | 14.9% |
| Renal Failure | 1.3% | 1.4% | 0.9% |
| Heart Failure | 1.0% | 0.9% | 0.6% |
| Body Mass Index (kg/meter$^2$) | 29.1±5.9 | 29.4±10.2 | 28.6±5.8 |
| Prior myocardial infarction | 8.0% | 7.2% | 5.5% |
| Prior cerebrovascular accident | 2.5% | 4.2% | 3.7% |
| Statins | 42.6% | 42.9% | 39.4% |
| Lipid lowering medication | 46.2% | 47.9% | 42.3% |
| ACE Inhibitor* | 31.0% | 35.1% | 27.3% |
| Beta-blocker* | 36.1% | 33.4% | 29.1% |
| Presentation | | | |
| Stable Angina | 56.6% | 59.4% | 62.6% |
| Unstable Angina | 29.0% | 26.2% | 26.6% |
| MI | 14.4% | 14.4% | 10.8% |

Death/MI event rates at 1, 3, and 5 years overall and among those with an HDL-C ≥ 40 mg/dL and < 40 mg/dL by tertiles of apolipoprotein A1.

| Overall (2,414) | | | | |
|---|---|---|---|---|
| | Tertile 1 | Tertile 2 | Tertile 3 | p-trend |
| 1 year | 8.9% | 5.7% | 5.9% | 0.02 |
| 3 year | 15.1% | 10.4% | 9.5% | <0.0001 |
| 5 year | 18.1% | 13.9% | 11.8% | <0.0001 |
| HDL-C ≥ 40 mg/dL (n=1,136) | | | | |
| 1 year | 12.2% | 7.1% | 5.2% | 0.001 |
| 3 year | 16.0% | 12.2% | 8.6% | 0.003 |
| 5 year | 21.1% | 14.9% | 11.0% | <0.0001 |
| HDL-C < 40 mg/dL (n=1,278) | | | | |
| 1 year | 7.7% | 4.6% | 7.4% | 0.52 |
| 3 year | 14.8% | 8.8% | 11.2% | 0.04 |
| 5 year | 17.0% | 12.9% | 13.6% | 0.11 |

FIG. 6

Multivariable associations of apolipoprotein A1 to death/MI at 1, 3, and 5 years stratified by HDL-C ≥ 40 mg/dL and <4 0 mg/dL.

HDL-C ≥ 40 mg/dL (n=1,136)

|  | Continuous | Tertile 2 vs. Tertile 1 | Tertile 3 vs. Tertile 1 |
| --- | --- | --- | --- |
| 1 year | HR=0.98, p=0.004 | HR=0.51, p=0.02 | HR=0.41, p=0.001 |
| 3 year | HR=0.99, p=0.005 | HR=0.67, p=0.09 | HR=0.51, p=0.003 |
| 5 year | HR=0.99, p=0.002 | HR=0.63, p=0.02 | HR=0.48, p<0.0001 |

HDL-C < 40 mg/dL (n=1,278)

|  | Continuous | Tertile 2 vs. Tertile 1 | Tertile 3 vs. Tertile 1 |
| --- | --- | --- | --- |
| 1 year | HR=0.99, p=0.42 | HR=0.62, p=0.13 | HR=1.06, p=0.86 |
| 3 year | HR=0.99, p=0.16 | HR=0.58, p=0.02 | HR=0.97, p=0.90 |
| 5 year | HR=0.99, p=0.30 | HR=0.80, p=0.23 | HR=0.98, p=0.94 |

FIG. 7

Death/MI event rates at 1, 3, and 5 years for tertiles of HDL-C, HDL$_2$, HDL$_3$, and VLDL-C.

| HDL-C | Tertile 1 (< 34) | Tertile 2 (34-43) | Tertile 3 (≥ 44) | p-trend |
|---|---|---|---|---|
| 1 year | 5.9% | 7.8% | 6.8% | 0.45 |
| 3 year | 11.3% | 12.2% | 11.5% | 0.92 |
| 5 year | 14.0% | 15.4% | 14.3% | 0.87 |
| HDL$_2$ | Tertile 1 (< 6) | Tertile 2 (6-7) | Tertile 3 (≥ 8) | |
| 1 year | 6.9% | 6.8% | 6.8% | 0.95 |
| 3 year | 12.8% | 11.0% | 11.3% | 0.39 |
| 5 year | 15.2% | 14.4% | 14.2% | 0.58 |
| HDL$_3$ | Tertile 1 (< 23) | Tertile 2 (23-28) | Tertile 3 (≥ 29) | |
| 1 year | 9.4% | 5.5% | 5.5% | 0.002 |
| 3 year | 16.3% | 9.5% | 9.1% | <0.0001 |
| 5 year | 19.1% | 12.8% | 11.8% | <0.0001 |
| VLDL-C | Tertile 1 (< 14) | Tertile 2 (14-19) | Tertile 3 (≥ 20) | |
| 1 year | 6.2% | 7.5% | 6.9% | 0.56 |
| 3 year | 10.9% | 13.0% | 11.1% | 0.86 |
| 5 year | 13.8% | 16.2% | 13.8% | 0.97 |

FIG. 8

Event rates (a) and longitudinal associations (b) of VAP and Abbott apolipoprotein A1 tertiles to death/MI at 1, 3, and 5 years among patients with Abbott apolipoprotein A1 results (n=1,478).

a.

| VAP | Tertile 1 (< 105.0) | Tertile 2 (105.0-119) | Tertile 3 (> 119.0) | p-trend |
|---|---|---|---|---|
| 1 year | 8.0% | 5.6% | 5.4% | 0.09 |
| 3 year | 14.5% | 9.3% | 9.3% | 0.008 |
| 5 year | 17.7% | 13.8% | 11.7% | 0.007 |
| Abbott | Tertile 1 (< 96.0) | Tertile 2 (96.0-112) | Tertile 3 (> 112.0) | p-trend |
| 1 year | 8.1% | 5.4% | 5.6% | 0.10 |
| 3 year | 14.2% | 8.8% | 10.1% | 0.04 |
| 5 year | 18.6% | 12.2% | 12.3% | 0.005 | b.

| VAP | Continuous | Tertile 2 vs. Tertile 1 | Tertile 3 vs. Tertile 1 |
|---|---|---|---|
| 1 year | HR=0.991, p=0.17 | HR=0.70, p=0.17 | HR=0.79, p=0.37 |
| 3 year | HR=0.989, p=0.04 | HR=0.61, p=0.01 | HR=0.72, p=0.10 |
| 5 year | HR=0.991, p=0.05 | HR=0.73, p=0.07 | HR=0.72, p=0.07 |
| Abbott | Continuous | Tertile 2 vs. Tertile 1 | Tertile 3 vs. Tertile 1 |
| 1 year | HR=0.997, p=0.54 | HR=0.73, p=0.21 | HR=0.94, p=0.80 |
| 3 year | HR=0.995, p=0.21 | HR=0.67, p=0.04 | HR=0.91, p=0.60 |
| 5 year | HR=0.994, p=0.06 | HR=0.69, p=0.03 | HR=0.80, p=0.21 |

METHODS FOR DETERMINING THE RISK OF CORONARY HEART DISEASE AND CLINICAL MANIFESTATIONS OF CORONARY HEART DISEASE

FIELD OF THE DISCLOSURE

The present disclosure relates generally to methods for measuring a risk of coronary heart disease or a clinical manifestation of coronary heart disease in a subject. The present disclosure relates specifically to methods for measuring a risk of coronary heart disease or a clinical manifestation of coronary heart disease by determining a concentration of apolipoprotein A1, $HDL_3$-C or a combination of the foregoing in a subject

BACKGROUND

Measurement of cholesterol levels has been known to be a predictor for various forms of coronary heart disease (CHD). The art has discovered that total cholesterol alone may not be adequate to identify subjects at risk for CHD and other conditions. For example, the predictive power of total cholesterol for risk of CHD diminishes in men with increasing age. In order to address this shortcoming, the measurement of various cholesterol fractions has been employed.

Measurement of various lipid parameters, whether alone or in combination, is known to correlate with various clinical outcomes, including, but not limited to, CHD, atherosclerosis, myocardial infarction and death. For example, plasma low density lipoprotein (LDL) and high density lipoprotein (HDL) cholesterol levels have been shown to be important risk factors for CHD. In addition, total serum cholesterol is strongly correlated with the incidence of atherosclerosis and coronary heart disease. Furthermore, increased levels of LDL cholesterol have been associated with the greater risk of CHD, while a strong inverse relationship exists between HDL cholesterol and the risk of CHD. Elevation of plasma VLDL is seen in survivors of myocardial infarction, suggesting the possible involvement of this lipoprotein in the atherosclerotic process.

As such, measurement of lipid parameters has become a valuable tool in the medical field. Recently, the distribution of cholesterol among all the lipoproteins (a lipoprotein cholesterol profile), in addition to total cholesterol, has been used to assess risk for coronary heart disease. Surprisingly, many patients remain at high residual risk even after "target" levels of lipids have been achieved.

To address this deficiency, the measurement of other parameters, such as apolipoprotein (apo) B (apo B) and apo A1, have been proposed for improving risk assessment. Apo B is the primary apolipoprotein of LDL, which is responsible for carrying cholesterol to tissues. While it is unclear exactly what functional role apo B plays in LDL, it is the primary apolipoprotein component and is absolutely required for LDL formation. Apo A1 is the major protein component of HDL in plasma and promotes cholesterol efflux from tissues to the liver for excretion. However, the predictive ability of these alternate parameters has not been adequately determined.

Therefore, the art is lacking methods to adequately predict the risk of CHD and/or clinical manifestations of CHD in a subject, particularly when the subject has reached target levels of one or more lipoproteins, such as, but not limited to, LDL or HDL or subclass of the foregoing. The present disclosure provides a solution to this need by providing methods to adequately predict the risk of CHD and/or clinical manifestations of CHD in a subject. In one embodiment, the method involves measuring the levels or concentration of apo A1, a subclass of HDL, specifically $HDL_3$-C, or a combination of the foregoing. The methods of the present disclosure are particularly useful when the subject has reached target levels of one or more lipoproteins, such as, but not limited to, LDL or HDL or subclass of the foregoing

BRIEF DESCRIPTION OF THE DRAWINGS

FIG. 3 shows longitudinal associations of apolipoprotein A1 tertiles to death/MI among those with an HDL-C≥40 mg/dL (log rank p-value=0.004) (FIG. 3A) and an HDL-C<40 mg/dL (log rank p-value=0.23) (FIG. 3B).

DETAILED DESCRIPTION

It is well established that elevated levels of LDL-C increase the risk of CHD and that this risk can be substantially reduced by lowering LDL-C (Third Report of the National Cholesterol Education Program (NCEP) Expert Panel on detection, evaluation, and treatment of high blood cholesterol in adults (Adult Treatment Panel III). *Circulation* 2002 106; 3143-3421). Therefore, LDL-C has become the target of cholesterol lowering therapy. However, significant residual risk remains even among those in whom LDL-C goals have been achieved (Alagona P., *Am J Manag Care* 2009; 15: S65-S73). In addition, selective screening for only individuals with elevated cholesterol levels may not adequately identify those in need of prevention (Abbott R D, et. al., *Arteriosclerosis* 1988; 8: 207-211). Several studies have shown that the residual risk in secondary prevention and the risk in primary prevention that cannot be accounted for by LDL-C may be attributable to abnormal levels of other lipoproteins (Arsenault B J, et al., *Nat Rev Cardiol* 2011; 8: 197-206). Among them, low levels of HDL-C have been shown to be powerful predictors of CHD in many prospective epidemiological studies (Miller N E, et. Al., *Lancet* 1977; 1: 965-968; Castelli W P, et al., *JAMA* 1986; 256: 2835-2838; Bersot T P, et al., *Am Heart J* 2003; 146: 1052-1059). It is estimated that for every 1 mg/dL increase in HDL-C there is an associated 2-3% lower risk in CHD (Asztalos B F., *Curr Opin Cardiol* 2004; 19: 385-391).

The protective effects of HDL are attributed to its anti-atherogenic functions, which include mediating reverse cholesterol transport, reducing inflammation in the arterial wall, inhibiting LDL oxidation, and enhancing endothelial function (Asztalos B F., *Curr Opin Cardiol* 2004; 19: 385-391; Shah P K., *Nat Rev Cardiol* 2001; 8: 187-188). Since increased levels of HDL-C have shown to have protective CHD effects (Rhodes G G, et al., *N Engl J Med* 1976; 294: 293-298), increasing HDL-C by therapeutic means appears to be a viable way of reducing CHD events. The Helsinki Heart Study was the first study to show the benefit of increasing HDL-C with gemfibrozil for CHD event reduction (Huttmen J K, et al., *Ann Med* 1991; 23: 155-159). It was reported that with each percent increase in HDL-C there was a 3% reduction in coronary events. The BECAIT (Bezafibrate Coronary Atherosclerosis Intervention Trial) showed a significant reduction in angiographic progression of CAD and this reduction was attributed to increase in HDL-C and reduction in triglycerides (Ericson C G, et. al., *Am J Cardiol* 1997; 80: 1125-1129). In the VA-HIT (Veterans Affairs High-Density Lipoprotein Cholesterol Intervention Trial), gemfibrozil increased HDL-C by 7.5% and decreased triglycerides by 24% resulting in a 22% reduction in primary clinical events (Rubins H B, et. al., *N Engl J Med* 1999; 341: 410-418). While the benefits of fibrates on CHD risk reduction by increasing HDL-C have been significant, effects of statins on CHD risk by their ability to increase HDL-C have been at best modest. For example, the LIPID (Long-Term Intervention with Pravastatin in Ischemic Disease) trial (The Long-Term Intervention with Pravastatin in Ischemic Disease (LIPID) Study Group, *N Engl J Med* 1998; 339: 1349-1357) which used pravastatin, and 4S (Scandinavian Simvastatin Survival Study) trial which used simvastatin, showed ~10% reduction in CHD events due to increases in HDL-C (Scandinavian Simvastatin Survival Study Group, *Lancet* 1994; 1344: 1383-1389). However, the CARE (Cholesterol and Recurrent Events) (Sacks F M, et al., *N Engl J Med* 1996; 335: 1001-1009) and WOSCOPS (West of Scotland Coronary Prevention Study) (Shepard J, et al., *N Engl J Med* 1995; 333: 1301-1307) studies showed no reduction in CHD events when HDL-C was increased. Niacin is another agent which has substantial effects on raising HDL-C (Elam M B, et al., *JAMA* 2000; 284: 1263-1270). However, it increases HDL-C not by increasing synthesis of HDL (i.e., number of HDL particles), but by decreasing catabolism of apo A1 (Kamanna VS, et al., *Curr Atheroscler Rep* 2000; 2: 36-46).

While past efforts to prevent coronary events by increasing HDL-C have shown promise, results of two recent trails have been disappointing. The recent announcement by the NHLBI to suddenly stop the AIM-HIGH (Atherothrobosis Intervention in Metabolic Syndrome with Low HDL/High Triglycerides: Impact on Global Health) study, which examined the effect of the combined therapy of simvastatin and niacin on CHD events, further raises doubts about the benefits of increasing HDL-C, specifically by means of niacin treatment (National Institutes of Health News May 26, 2011). Furthermore, the ILLUMINATE (Investigation of Lipid Level Management to Understand its Impact in Atherosclerotic Events) trial in which torcetrapib, a cholesterol ester transport protein (CETP) inhibitor, was used to increase HDL-C was also stopped abruptly due to a 25% increase in CHD events in the treatment arm of the study (Barter P J, et. al., *N Engl J Med* 2007; 357: 2109-2122). The inconsistency of these results about the benefit of raising HDL-C for CHD event reduction may suggest that the efficacy of reverse cholesterol transport may not depend upon how much cholesterol each HDL particle carries but rather on the type and number of HDL particles.

HDL is a complex lipoprotein with multiple atheroprotective functions. Apo A1 is its major protein, constituting 70% of the HDL protein mass, and is located on the surface of all HDL particle types. HDL is a highly heterogeneous particle in terms of its size, density, charge, chemical composition, and functionality. Traditionally, HDL has been separated into two density subclasses, $HDL_2$ (large, buoyant lipid rich particle) and $HDL_3$ (small, dense and relatively lipid poor particle) by ultracentrifugation. The unique structural arrangement of apo A1 confers unique biological functions to it. In fact, the anti-atherogenic properties of HDL, including reverse cholesterol transport, are assumed to be due to apo A1 being the structural component of the HDL particle (Shah P K., *Nat Rev Cardiol* 2001; 8: 187-188). Furthermore, some mutations of apo A1, such as apo $A1_{Milano}$, are known to protect from CHD even in the presence of low HDL-C, thus supporting the protective role of apo A1 (Franceschini G, *J Clin Invest* 1980; 66: 892-900).

Thus, there is evidence to suggest that it is apo A1 which plays an important role in conferring atheroprotective effects of HDL particle, not necessarily the amount of cholesterol it carries. Several studies have demonstrated that measurement of HDL subclasses might improve the prediction of CHD risk (Gofman J W, et al., *Circulation* 1966; 34: 679-697; Miller N E, et. al., *Br Med J* 1981; 282: 1741-1744). However, their predictive abilities have varied.

The present disclosure provides for apo A1 as a novel indicator for predicting the risk of CHD and clinical manifestations of CHD, such as death and myocardial infarction. The data presented show apo A1 was strongly and inversely associated with D/MI, while HDL-C showed no association in our study. Furthermore, the present disclosure provides for $HDL_3$-C as a novel indicator for predicting the risk of CHD and clinical manifestations of CHD, such as death and myocardial infarction. The data presented show $HDL_3$-C to be significantly and inversely associated with the presence of angiographic CAD and D/MI. These associations were not observed for $HDL_2$-C.

In a first aspect, the present disclosure provides a method of measuring the risk of CHD or a clinical manifestations of CHD in a subject, the method comprising, consisting of or consisting essentially of, determining the concentration of apo A1 in a subject.

In a second aspect, the present disclosure provides a method of measuring the risk of CHD or a clinical manifestations of CHD in a subject, the method comprising, consisting of or consisting essentially of, determining the concentration of apo A1 in a subject and transforming the concentration of apo A1 to a measure of risk based on a predetermined risk function.

In a third aspect, the present disclosure provides a method of measuring the risk of CHD or a clinical manifestations of CHD in a subject, the method comprising, consisting of or consisting essentially of, determining the concentration of apo A1 in a subject and transforming the concentration of apo A1 to a measure of risk based on a predetermined risk function wherein the risk function comprises comparing the concentration of apo A1 to a predetermined threshold concentration of apo A1, and determining the presence of an elevated risk if the concentration of apo A1 determined for the subject is below or above the threshold concentration.

In a fourth aspect, the present disclosure provides a method of measuring the risk of CHD or a clinical manifestations of CHD in a subject, the method comprising, consisting of or consisting essentially of, determining the concentration of $HDL_3$-C in a subject.

In a fifth aspect, the present disclosure provides a method of measuring the risk of CHD or a clinical manifestations of CHD in a subject, the method comprising, consisting of or consisting essentially of, determining the concentration of HDL$_3$-C in a subject and transforming the concentration of HDL$_3$-C to a measure of risk based on a predetermined risk function.

In a sixth aspect, the present disclosure provides a method of measuring the risk of CHD or a clinical manifestations of CHD in a subject, the method comprising, consisting of or consisting essentially of, determining the concentration of HDL$_3$-C in a subject and transforming the concentration of HDL$_3$-C to a measure of risk based on a predetermined risk function wherein the risk function comprises comparing the concentration of HDL$_3$-C to a predetermined threshold concentration of HDL$_3$-C, and determining the presence of an elevated risk if the concentration of HDL$_3$-C determined for the subject is below or above the threshold concentration.

In a seventh aspect, the present disclosure provides a method of measuring the risk of CHD or a clinical manifestations of CHD in a subject, the method comprising, consisting of or consisting essentially of, determining the concentration of apo A1 and HDL$_3$-C in a subject.

In an eighth aspect, the present disclosure provides a method of measuring the risk of CHD or a clinical manifestations of CHD in a subject, the method comprising, consisting of or consisting essentially of, determining the concentration of apo A1 and HDL$_3$-C in a subject and transforming the concentration of apo A1 and HDL$_3$-C to a measure of risk based on a predetermined risk function.

In a ninth aspect, the present disclosure provides a method of measuring the risk of CHD or a clinical manifestations of CHD in a subject, the method comprising, consisting of or consisting essentially of, determining the concentration of apo A1 and HDL$_3$-C in a subject and transforming the concentration of apo A1 and HDL$_3$-C to a measure of risk based on a predetermined risk function wherein the risk function comprises comparing the concentration of apo A1 and HDL$_3$-C to a predetermined threshold concentration of apo A1 and HDL$_3$-C, and determining the presence of an elevated risk if the concentration of apo A1 and HDL$_3$-C determined for the subject is below or above the threshold concentration.

In any of the first through third and seventh through ninth aspects, the apo A1 concentration is determined from the measured values of one or more lipoprotein cholesterol fractions (i.e., the apo A1 concentration is not measured directly). In a specific embodiment of the first through third and seventh through ninth aspects, the apo A1 concentration is determined from the measured values of one or more of the HDL$_2$-C, HDL$_3$-C and VLDL-C concentrations in the subject. In a further specific embodiment of the first through third and seventh through ninth aspects, the apo A1 concentration is determined from the measured values of each of HDL$_2$-C, HDL$_3$-C and VLDL-C concentrations from the subject. In still a further embodiment of the first through third and seventh through ninth aspects, the apo A1 concentration is determined from the measured values of HDL$_2$-C and HDL$_3$-C, HDL$_2$-C and VLDL-C or HDL$_3$-C and VLDL-C. In yet a further embodiment of the first through third and seventh through ninth aspects, the apo A1 concentration is determined from the measured values of HDL$_2$-C and HDL$_3$-C, HDL$_2$-C and VLDL, HDL$_3$-C and VLDL, one of HDL$_2$-C, HDL$_3$-C and VLDL or each of HDL$_2$-C, HDL$_3$-C and VLDL plus the measured value of at least one of the following: total HDL-C, total LDL-C, LDL-R, Lp(a), IDL-C, apoB, total triglycerides, VLDL$_{1+2}$-C, VLDL$_3$-C, total cholesterol, total non-HDL cholesterol, remnant lipoproteins, or LDL density pattern. In still a further embodiment of the first through third and seventh through ninth aspects, the apo A1 concentration is determined without measuring total HDL-C, total LDL-C, LDL-R, Lp(a), IDL-C, apoB, total triglycerides, VLDL$_{1+2}$-C, VLDL$_3$-C, total cholesterol, total non-HDL cholesterol, remnant lipoproteins, or LDL density pattern. In yet a further embodiment of the first through fourth aspects, the apo A1 concentration is determined by direct measure apo A1 concentration.

In any of the fourth through ninth aspect, the concentration of HDL$_3$-C is determined using the VAP assay as described herein.

In any of the first through ninth aspects, the risk of CHD or a clinical manifestation of CHD is determined in a subject with normal HDL-C levels (≥40 mg/dL).

In any of the first through ninth aspects, a clinical manifestation of CHD includes, but is not limited to, death, atherosclerosis and myocardial infarction (MI)

In any of the first through ninth aspects, the threshold concentration of apo A1 or HDL$_3$-C may be specifically determined for both male and female together or for a male or a female individually.

The present disclosure provides a method to adequately predict the risk of CHD and clinical manifestations of CHD. In one embodiment, the method comprises, consists of or consists essentially of, determining the levels of apo A1 in a subject.

The apo A1 determining step may be carried out indirectly, through the measurement of the concentration of one or more surrogate markers or may be carried out directly by measuring the concentration of apo A1. When the determining step is carried out indirectly, the one or more surrogate markers may be lipoprotein cholesterol fractions, such as those determined using cholesterol testing kits and methods. In a particular embodiment, the surrogate markers are at least one of the lipoprotein cholesterol fractions HDL$_2$-C, HDL$_3$-C and VLDL-C. In a further particular embodiment, the surrogate markers are the lipoprotein cholesterol fractions HDL$_2$-C, HDL$_3$-C and VLDL-C. In still a further embodiment, the surrogate markers are HDL$_2$-C and HDL$_3$-C, HDL$_2$-C and VLDL-C or HDL$_3$-C and VLDL-C. In yet a further embodiment of the first through third and seventh through ninth aspects, the apo A1 concentration is determined from the measured values of HDL$_2$-C and HDL$_3$-C, HDL$_2$-C and VLDL-C or HDL$_3$-C and VLDL-C, HDL$_2$-C, HDL$_3$-C and VLDL or each of HDL$_2$-C, HDL$_3$-C and VLDL-C plus the measured value of at least one of the following: total HDL-C, total LDL-C, LDL-R, Lp(a), IDL-C, apoB, total triglycerides, VLDL$_{1+2}$-C, VLDL$_3$-C, total cholesterol, total non-HDL cholesterol, remnant lipoproteins, or LDL density pattern. In still a further embodiment, the surrogate markers do not include total HDL$_2$-C, HDL$_3$-C and VLDL or each of HDL$_2$-C, HDL$_3$-C and VLDL-C plus the measured value of at least one of the following: total HDL-C, total LDL-C, LDL-R, Lp(a), IDL-C, apoB, total triglycerides, VLDL$_{1+2}$-C, VLDL$_3$-C, total cholesterol, total non-HDL cholesterol, remnant lipoproteins, or LDL density pattern.

In the present disclosure, the concentration of the lipoprotein cholesterol fractions are determined using the Vertical Auto Profile method (Atherotech, Birmingham, Ala.), although other methods may also be used. When direct measurement of apo A1 is used, any method known in the art to measure apo A1 may be used, including, but not limited to, immunological methods.

In one embodiment, the concentration of apo A1 is determined using the concentration of the surrogate markers HDL$_2$-C, HDL$_3$-C and VLDL-C by applying these surrogate marker concentrations to the formula:

Calculated apo $A1=[(2.4591*HDL_3\text{-}C)+(0.611*HDL_2\text{-}C)+(0.555*VLDL\text{-}C)+33.75]$ The formula was developed by stepwise forward multiple linear regression using lipoprotein cholesterol classes and subclasses values. It was determined that only HDL$_2$-C, HDL$_3$-C and VLDL-C lipoprotein cholesterol subclasses contributed significantly to the apo A1 determination (r=0.93). The formula was verified by comparing calculated values with directly measured apo A1 concentration.

In another embodiment, the method of predicting the risk of CHD and clinical manifestations of CHD comprises, consists of or consists essentially of, determining the levels of $HDL_3$-C in a subject. The $HDL_3$-C determining step may be carried out indirectly, through the measurement of one or more surrogate markers or may be carried out directly by measuring the concentration of $HDL_3$-C. In one embodiment, the concentration of $HDL_3$-C is measured using the VAP assay as described herein.

In one embodiment of the above method, a sample is obtained from the patient. The sample may be a blood sample obtained from the patient. The blood sample may be collected and processed as is known in the art. In one embodiment, the blood samples are collected in an anti-chelating agent such as EDTA or another calcium binding agent. The blood sample may be subject to purification, such as, but not limited to, centrifugation, in order to separate the plasma fraction from other components of the blood such as, but not limited to, DNA. The blood sample may be stored at 4 degrees Celsius or lower prior to the purification step if desired. The plasma portion may be stored cryogenically after purification for future analysis.

In an alternate embodiment, the method of measuring the risk of CHD and clinical manifestations of CHD in a subject comprises, consists or consists essentially of determining the concentration of apo A1, $HDL_3$-C or a combination of the foregoing in a subject as discussed above and transforming the concentration of apo A1, $HDL_3$-C or a combination of the foregoing to a measure of risk based on a predetermined risk function.

In the description that follows, reference will be made to apo A1. However, the description below is equally applicable to $HDL_3$-C. In one embodiment, the predetermined risk function comprises comparing the concentration of apo A1 from the subject to a predetermined threshold concentration of apo A1, and determining the presence of an elevated risk if the concentration of apo A1 determined for the subject is below the threshold concentration. In another embodiment, the predetermined risk function comprises comparing the concentration of apo A1 from the subject to a predetermined threshold concentration of apo A1, and determining the presence of no elevated risk if the concentration of apo A1 determined for the subject is equal to or above the threshold concentration. The threshold concentration may be different for subjects of difference sex or age or may be different depending on one or more stratification criterion (discussed below).

The threshold concentration may be determined in a variety of ways. In one embodiment, the threshold concentration is determined experimentally. In an alternate embodiment, the threshold concentration is determined by reference to a standard prepared by a governmental or non-governmental body or agency or values in the scientific literature. In a further alternate embodiment, the threshold concentration may be determined by comparison to a comparative database.

In one embodiment, the threshold concentration is determined empirically or experimentally. In one embodiment, the threshold concentration is determined to be an apo A1 concentration<100 mg/dL, <105 mg/dL, <110 mg/dL, or <115 mg/dL. In an alternate embodiment, the threshold concentration is determined to be an apo A1 concentration<105.6 mg/dL or an apo A1 concentration between 105.7 and 120 mg/dL. In a specific embodiment, the threshold concentration is determined to be an apo A1 concentration<105.6 mg/dL. In a further specific embodiment, the threshold concentration is determined to be an apo A1 concentration<145 mg/dL when the subject is female and <118 mg/dL when the subject is male.

When a standard prepared by a governmental or non-governmental body or agency is used to determine the threshold concentration, the threshold concentration is determined from that standard. A number of standards known in the art may be used.

When a comparative database is used to determine the threshold concentration, the comparative database may be constructed in a variety of ways. The individuals in the comparative database may be age matched to the subject, or may be non-aged matched as compared to the subject. For example, if the subject is 65 years of age, in one embodiment the comparative database may be composed of individuals with ages from, for example, 60 to 70 years, or in a second embodiment, the comparative database may be composed of individuals with ages from, for example, 25 to 40 years. The use of a comparative database comprising a younger population may offer certain advantages since the younger subjects that comprise the population will be more likely to be free of disease states and other conditions that may impact the analysis. Using an age matched population for the comparison may actually decrease the sensitivity of the method since the age matched population of the comparative database may in fact have a certain risk for CHD or a clinical manifestation or coronary heart disease.

The individuals making up the comparative database may be healthy (i.e., disease free) or they may be selected based on their diagnosis of CHD or a clinical manifestation of CHD, or both. If healthy individuals are selected, the apo A1 concentration determined from the subject can be compared with the apo A1 concentration for the healthy individuals. If individuals with a diagnosed disease state are selected, the apo A1 concentration determined from the subject can be compared with the corresponding apo A1 concentration for the individuals diagnosed with a disease states and/or defined stages of a disease state. In this manner, the comparison may be able to predict if a subject is at risk for CHD or a clinical manifestation of CHD (from a comparison with healthy individuals in the comparative database), if the subject is suffering from CHD or a clinical manifestation of CHD (from a comparison with individuals in the comparative database diagnosed with CHD or a clinical manifestation of CHD) or to diagnose severity (from a comparison with individuals in the comparative database diagnosed with various stages of CHD or a clinical manifestation of CHD). The stratification of the database, as discussed below, may aid in making such comparisons.

The comparative database may be stratified based on a number of stratification criteria. These criteria may be risk factors (including those risk factors provided in FIG. 4 and elsewhere in the present disclosure), demographic factors, other relevant factors or a combination of the preceding. Examples, of risk factors include, but are not limited to, age, HDL level, hypertension, hyperlipidemia, diabetes, family history of coronary artery disease, smoking status, renal failure, heart failure, body mass index (kilograms/$m^2$), prior MI, prior CVA, statin use, use of lipid lowering medication, use of an AQCE inhibitor, use of a beta-blocker use and status with regard to health conditions (for example presentation with stable angina, unstable angina or MI). Other risk factors may also be included. Demographic factors include, but are not limited to, gender and ethnicity. The inclusion of a specific stratification criteria as a risk factor or demographic factor may be modified (for example, age may be considered both a risk factor and a demographic factor). In one embodiment, a stratification criterion includes HDL-C levels greater than or equal to 40 mg/dL or HDL-C levels less than 40 mg/dL. The individuals in the comparative database may be tagged or otherwise identified, such that the appropriate population of individuals in the comparative database may be selected for the comparison to the subject.

Furthermore, the comparative database may be refined over time. The individuals in the database may be followed over time and their health status monitored. If an individual no longer meets an inclusion criterion for the comparative database, the individual may be removed or their information modified. In this manner the quality of the comparative database may be improved over time, resulting in a database with improved sensitivity and specificity.

The concentration of apo A1 determined from the subject may then be compared to the concentration of apo A1 from appropriately selected individuals in a comparative database. Appropriately selected means that the apo A1 concentration from a defined group of individuals in the comparative database is selected for comparison to the apo A1 concentration determined for the subject. The defined group may be all the individuals in the comparative database or less than all the individuals in the comparative database. The defined group may be selected on the basis of stratification criteria as discussed above. The healthcare provider may select the defined group, with such selection based on one or more defining characteristics of the subject. For example, if the subject is a 60 year old, non-smoking, Caucasian male suspected of having CHD or a clinical manifestation of CHD, the stratification criteria may be used to select the defined group from the comparative database for the comparison step. In one embodiment, the defined group may be selected on the basis of ethnicity (Caucasian), gender (male), health status (disease free or diagnosed with CHD or a clinical manifestation of CHD), age (20-45 years of age or 55-65 years of age) and HDL-C levels over 40 mg/dL. Furthermore, the comparison may be carried out multiple times for any given subject to various iterations of the comparative database. For example, given the same 60 year old, non-smoking, Caucasian male subject, a second comparison could be made using a defined group from the database selected on the basis of gender (male) only, or selected to include all individuals in the comparative database.

Methods

Study Patients

Study patients (N=2,414) were drawn from the Intermountain Heart Collaborative Study (IHCS) (Taylor G S, et al., *Am Heart J* 1998; 136: 792-803). The IHCS is a cardiac catheterization registry that includes patients undergoing angiography at an Intermountain Healthcare hospital (LDS. Hospital: Salt Lake City, Utah; Intermountain Medical Center, Murray, Utah; and McKay Dee Hospital, Ogden Utah). At the time of angiography, patients who provided informed consent had a blood sample taken and stored cryogenically for future testing. Patients were included in this study if they were ≥18 years of age, gave written informed consent, and had lipid panel results available from hospitalization. The Intermountain Healthcare Urban Central Institutional Review Board approved this study.

Other Risk Factors, Demographic Information, and Clinical Assessments

In addition to age and gender, patient information collected included diabetes status (WHO criteria: fasting blood glucose>125 mg/dL, clinical diagnosis of diabetes mellitus, or anti-diabetic medication use) (World Health Organization: Definition and diagnosis of diabetes mellitus and intermediate hyperglycemia. Report of a World Health Organization/International Diabetes Federation Consultation. Geneva, World Health Organization, 2005), hypertension (systolic blood pressure≥140 mmHg, diastolic≥90 mmHg, or antihypertensive medication use), renal failure (clinical diagnosis or GFR<15 ml/min), hyperlipidemia (total cholesterol≥200 mg/dL, LDL≥130 mg/dL, or, cholesterol-lowering medication use), and congestive heart failure (clinical diagnosis or physician-reported). Family history was patient-reported if a first-order relative had suffered cardiovascular death, MI, or coronary revascularization before age 65 years. Smoking included active smokers or those with a >10 pack-year history. Clinical presentation included stable angina (stable exertional symptoms only), unstable angina (progressive symptoms or symptoms at rest), or acute MI (creatinine kinase-MB>6 mg/dL and creatinine kinase-MB index>3%). Treatment type was defined as treatment with medication only, percutaneous coronary intervention, or coronary artery bypass surgery. Admission and discharge medications (i.e., statin, other lipid lowering medications, ace-inhibitors [ACEI], aspirin, angiotensin receptor blocker [ARB], beta-blocker, clopidogrel, diuretic) were also available.

Significant coronary artery disease (CAD) was defined as the presence of one or more ≥70% obstructive lesions by coronary angiography. Assessment of CAD was made by review of angiograms by the patient's cardiologist, and results were entered into the computer database in a format modified after the coronary artery surgery study protocol (Anonymous, *N Engl J Med* 1984; 310(12): 750-8). On the basis of angiographic evaluation, the patients were determined to have single-, double-, or triple-vessel disease as defined by the presence of a 70% stenosis in each major vessel counted, with the left main counting as two vessels. Assessment of CAD was performed blinded to results of blood testing.

Figure 4:
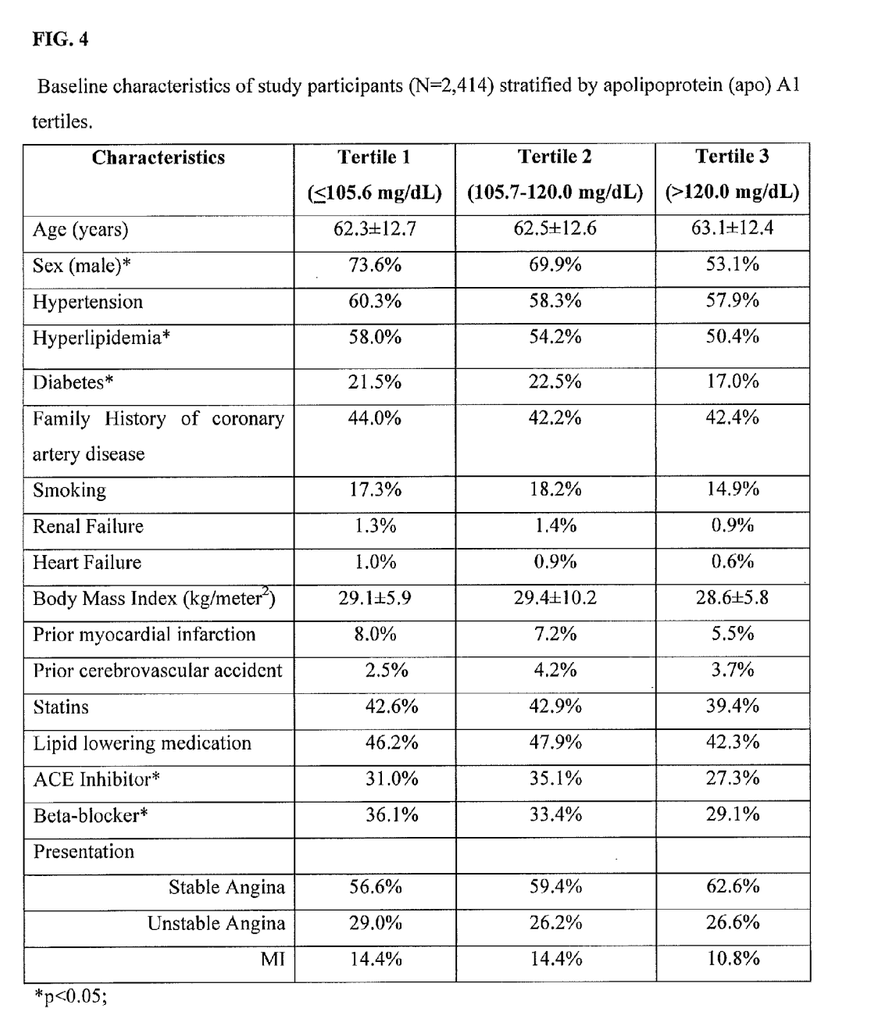
FIG. 4 shows baseline characteristics of study participants (N=2,414) stratified by apolipoprotein A1 tertiles.

Patient characteristics for the tertiles (T1-T3) of apo A1 are shown in FIG. 4.

Patient Follow-Up and Event Assessment

Average length of follow-up was 3.7±2.3 years. Events included the composite outcome of death and MI at 1 year, 3 years, and 5 years. MI was defined as a hospitalization where a patient has a troponin I level≥0.4 ng/mL or a discharge diagnosis of an MI (ICD-9 code 410). Deaths were determined by telephone survey, hospital records, and Utah State Health Department records (death certificates) and were verified through Social Security death records. Patients not listed as deceased in any registry were considered as alive.

Lipoprotein Subclass Quantification

At the time of angiography, blood samples were collected in EDTA and refrigerated at 4° C. Within 24 hours, samples were centrifuged and plasma and DNA were separated and stored cryogenically. Cholesterol concentrations of lipoprotein classes [HDL-C, LDL-C, intermediate density lipoprotein cholesterol (IDL-C), very low density lipoprotein cholesterol (VLDL-C), and lipoprotein(a) (Lp(a)) and subclasses (including $HDL_2$-C and $HDL_3$-C) were measured using the Vertical Auto Profile (VAP) method (Atherotech; Birmingham, Ala.). The VAP method separates lipoproteins based on their density using single vertical spin density gradient ultracentrifugation (Kulkarni K R, et al., *J Lipid Res* 1994; 35: 159-168; Kulkarni K R., *Clin Lab Med,* 2006; 26: 787-802; the foregoing references are incorporated herein by reference for the teaching of the VAP method). Apo A1 was estimated by the VAP method using the procedure described previously (Kulkarni K R, et al., *Diab Vasc Dis Res* 2007; 4: 266; the foregoing reference is incorporated herein by reference for the teaching of the apo A1 measurement method). Briefly, the procedure involved developing an equation to calculate apo A1 based upon a stepwise forward multiple regression analysis model. Apo A1 measured from immunoassay method (Architect/C8000 chemistry analyzer by Abbott Diagnostics) from 204 unselected patient specimens (training set) received by Atherotech was used as a dependent variable and cholesterol concentrations of various lipoprotein classes and subclasses (HDL-C, $HDL_2$-C, $HDL_3$-C, LDL-C, Lp(a), IDL-C, VLDL-C, LDL-C peak maximum time which is inversely proportional to the density of LDL, non HDL-C, total cholesterol, and triglycerides) obtained from the VAP method using the same 204 patient serum specimens as independent variables. The model with the fewest number of independent variables which gave the highest r (correlation coefficient) was used to develop regression equation to estimate apo A1. The model that fit these criteria included HDL-C subclasses ($HDL_2$-C and $HDL_3$-C) and VLDL-C with an r value of 0.93. Based upon this model the following equation was established to estimate apo A1.

$$\text{VAP estimated apo } A1 = [(2.4591*HDL_3\text{-}C) + (0.611*HDL_2\text{-}C) + (0.555*VLDL\text{-}C) + 33.75]$$

The above equation was further verified by comparing VAP estimated apo A1 with immunoassay measured apo A1 using a new set of 1,058 fresh patient serum specimens (test set) with the following results: mean±SD for immunoassay apo A1, 156.9±28.3 mg/dL; mean±SD for VAP estimated apo A1, 153.3±25.7 mg/dL; bias, −2.3%; slope, 0.83; intercept=22.9 mg/dL; r, 0.92; and standard error of estimate, 10.3 mg/dL.

Apo A1 was estimated for all 2,414 patients selected from IHCS registry using the above equation. Apo A1 was also measured directly using the same immunoassay in 1,478 of the 2,414 patients to confirm the results obtained using VAP estimated apo A1. Apo A1 was evaluated as a continuous variable and as tertiles [tertile 1 (n=800): <105.5 mg/dL; tertile 2 (n=801): 105.5-120.0 mg/dL; and tertile 3 (n=813): >120.0 mg/dL], with higher levels being desirable.

Statistical Analysis

The chi-square test, student's t test, and the analysis of variance (ANOVA) were used to examine tertiles of apo A1 to baseline characteristics. To confirm the associations of the composite outcome of D/MI determined by univariable analysis, multivariable Cox hazard regression (SPSS, version 15.0; Chicago, Ill.) was performed to determine hazard ratios (HRs). Available baseline risk factors used in the modeling included age, gender, hypertension, hyperlipidemia, diabetes status, smoking, family history of CAD, renal failure, number of diseased vessels, treatment type, prior MI, prior CVA, congestive heart failure, presentation (stable angina, unstable angina, or acute MI), number of vessels with stenosis≥70%, and admission and discharge medications. Final models entered significant and confounding covariables. Two-tailed p-values are presented with 0.05 designated as nominally significant.

Results

Patient Characteristics

A total of 2,414 patients were studied. The average apo A1 level among the entire cohort was 114.5±18.2 (range: 63.6-200.3) mg/dL. Apo A1 was highly correlated with HDL-C (r=0.966, p<0.0001) and its subclasses, $HDL_2$-C (r=0.708, p<0.0001) and $HDL_3$-C (r=0.973, p<0.0001). Patient characteristics for the tertiles (T1-T3) of apo A1 are shown in FIG. 4. The percent of patients that were male, had hyperlipidemia, diabetes, and were taking ACEI or beta-blockers was significantly different among the tertiles. Higher frequencies were found in tertile 1 and lower values in tertile 3, suggesting an inverse association of apo A1 with these CHD risk parameters. Apo A1 was also associated with a step-wise increase in the diagnosis of CAD based on angiographic evaluation with each decreasing tertile (T1=57.9%, T2=54.9%, and T3=48.8%, p-trend<0.0001).

Long-Term Outcomes

Figure 1:
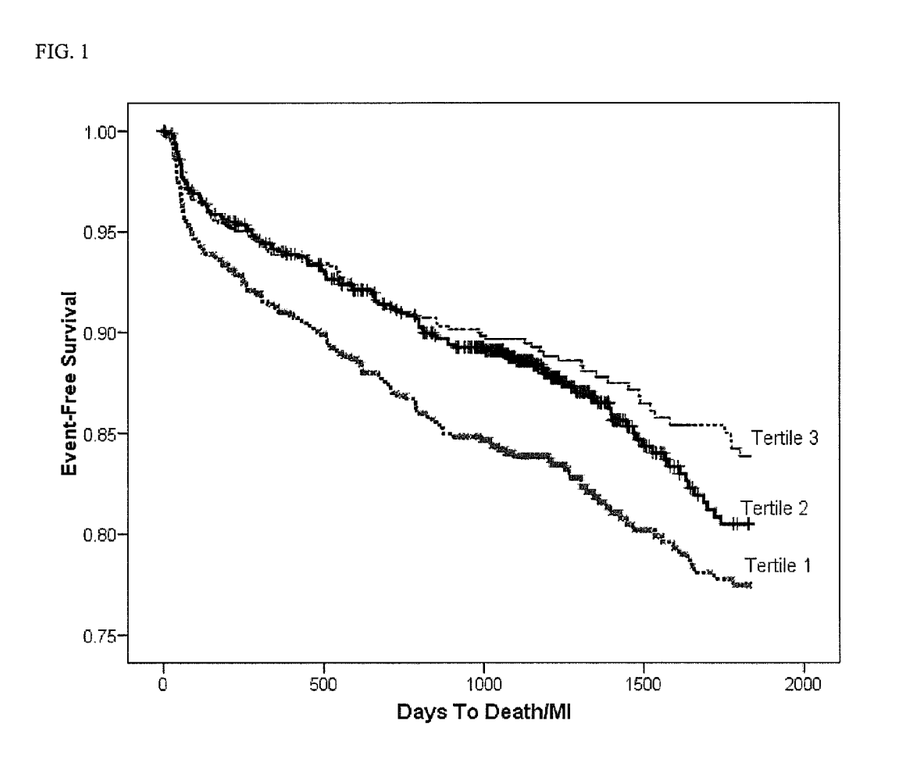
FIG. 1 shows longitudinal associations of apolipoprotein A1 tertiles to death/MI (log rank p-value=0.005)
Figure 2:
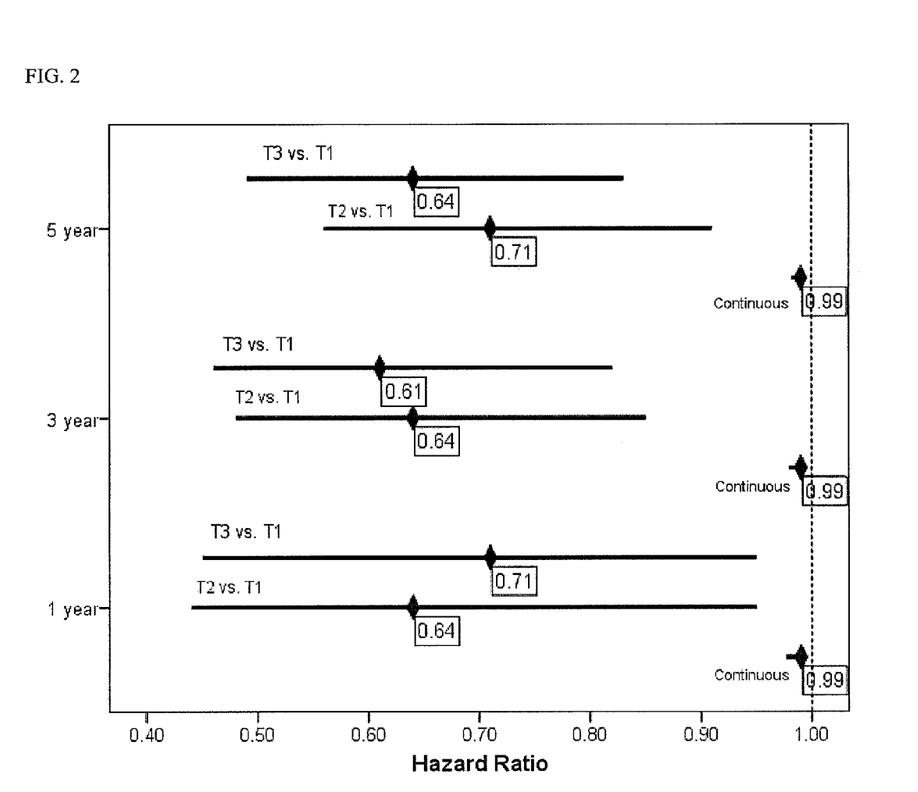
FIG. 2 shows adjusted hazard ratios (HR) and p-values for apolipoprotein A1 as a continuous and as tertiles for 1 year, 3 year, and 5 year death/MI.
Figure 5:
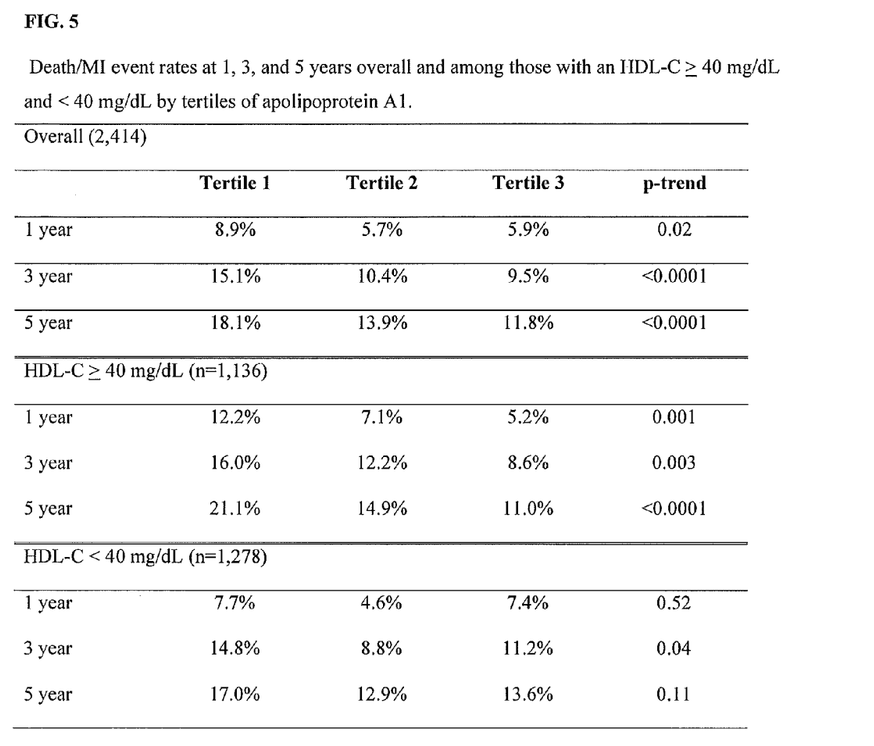
FIG. 5 shows death/MI event rates at 1, 3, and 5 years overall and among those with an HDL-C≥40 mg/dL and <40 mg/dL by tertiles of apolipoprotein A1 (N=2,414).

D/MI event rates at 1, 3, and 5 years for apo A1 tertiles among the entire cohort are shown in FIG. 5 (top section). At all time points, D/MI frequencies were significantly different among the 3 tertiles, with T1 having the highest and T3 having the lowest D/MI rates. These results suggest an inverse relationship between apo A1 levels and D/MI rate (i.e., lower the apo A1 level the higher the D/MI rate). A total of 401 (16.6%) events occurred during the entire length of follow-up, with a greater number taking place in T1 (T1=160 [20.0%], T2=125 [15.6%], T3=116 [14.3%], p-trend=0.002). Longitudinal associations of apo A1 tertiles with D/MI are shown in FIG. 1 (Kaplan-Meier event-free survival curves). The event-free survival rate was higher among patients in T3 (highest apo A1 levels). When evaluated as continuous and tertiled variables using Cox regression analysis, higher apo A1 was associated with a significant decrease in the risk of D/MI at all time points, even after adjustment (FIG. 2). These associations persisted, with little attenuation, after adjustment by LDL-C.

Predictive Ability of Apo A1 Among Patients Stratified by HDL-C Levels

Apo A1 is the major protein component of the HDL-C particle and its serum concentration is highly correlated with serum HDL-C concentration. Therefore, it was evaluated whether there is superiority or equal predictive ability between the two. Tertiles (T1: <34 mg/dl, T2: 34-43 mg/dl, T3: ≥44 mg/dl) of HDL-C were found to be significantly (p-trend<0.0001) associated with angiographically determined CAD in a stepwise manner, with low levels having increased risk: ≤34 mg/dL=59.6%, 35-44 mg/dL= 56.6%, >44 mg/d=44.9%). However, HDL-C was not predictive of 1, 3, or 5 year D/MI when evaluated as a continuous or tertiled variable.

As with LDL-C, determining at-risk individuals when one or more traditional risk factors are not present is essential (i.e., when HDL-C is 40 mg/dL). Therefore, we evaluated the predictive ability of apo A1 among those with "normal" (HDL-C mg/dL) and "abnormal" (HDL-C<40 mg/dL) levels. A total of 47.1% (n=1,136) of the study population had normal HDL-C. FIG. 5 shows the graded associations of apo A1 tertiles for 1, 3, and 5 year D/MI event rates stratified by HDL-C (HDL-C≥40 mg/dL and HDL-C<40 mg/dL). At all time points, apo A1 was significantly inversely associated with D/MI among those with HDL-C≥40 mg/dL. However, apo A1 did not show graded associations with 1 and 5 year D/MI among study subjects with an HDL-C<40 mg/dL, though significance was marginally achieved at 3 years.

Figure 3A:
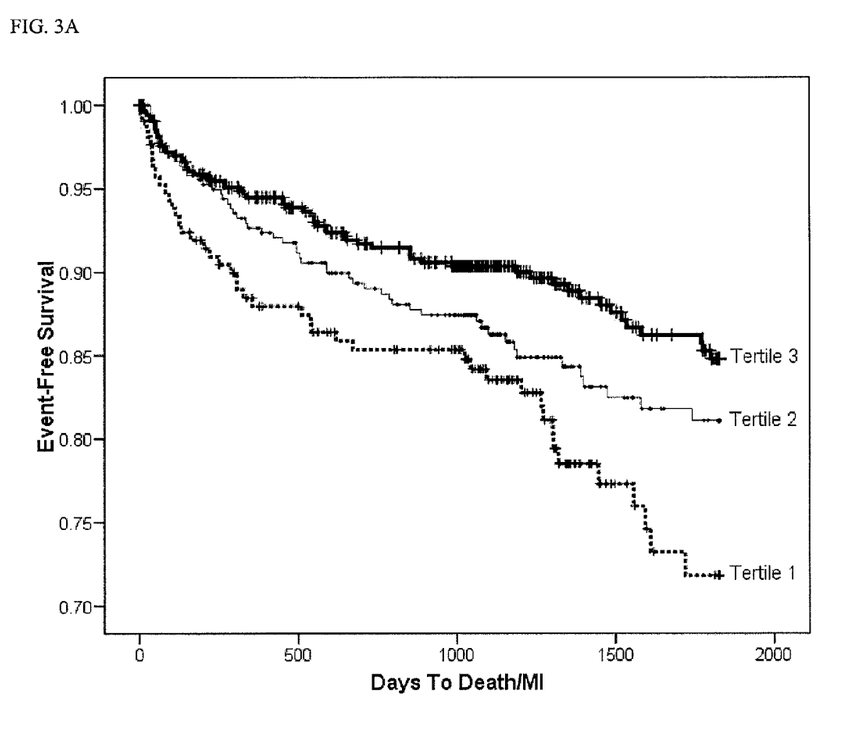
Figure 3B:
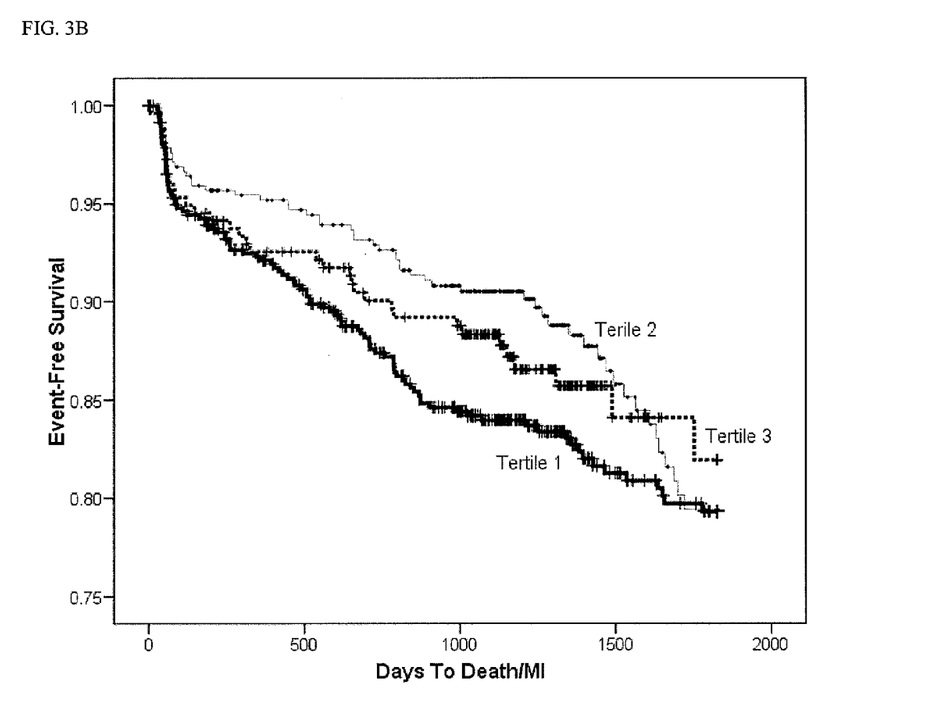
Figure 6:
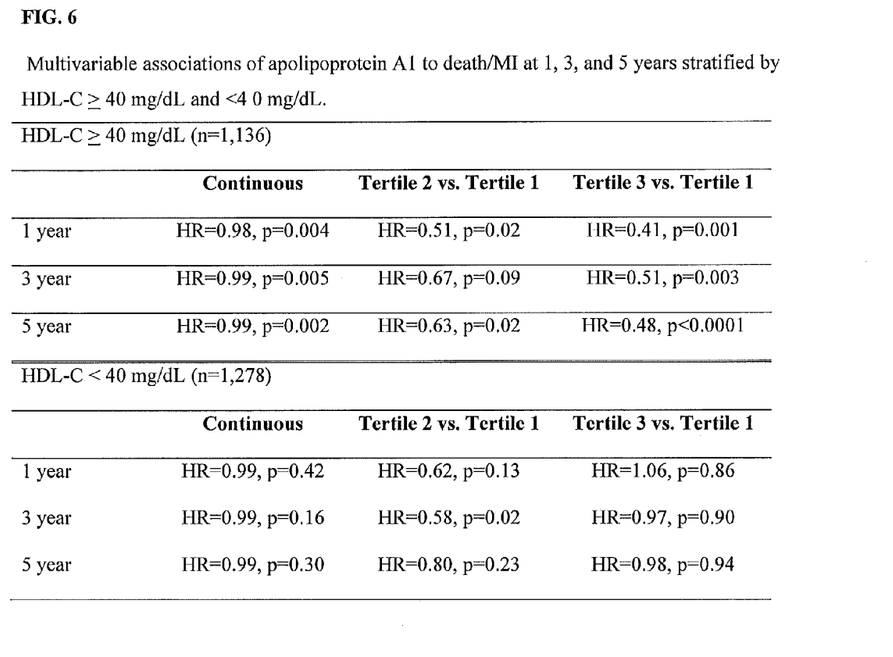
FIG. 6 shows multivariable associations of apolipoprotein A1 to death/MI at 1, 3, and 5 years stratified by HDL-C≥40 mg/dL and <40 mg/dL.

FIG. 3 displays longitudinal associations of apo A1 tertiles to death/MI stratified by HDL-C levels. After adjustment, both the continuous and tertiled apo A1 was significantly associated with 1, 3, and 5 year D/MI among those with an HDL-C≥40 mg/dL (FIG. 6). However, among those with an HDL-C<40 mg/dL, these associations were not present (FIG. 6).

Figure 7:
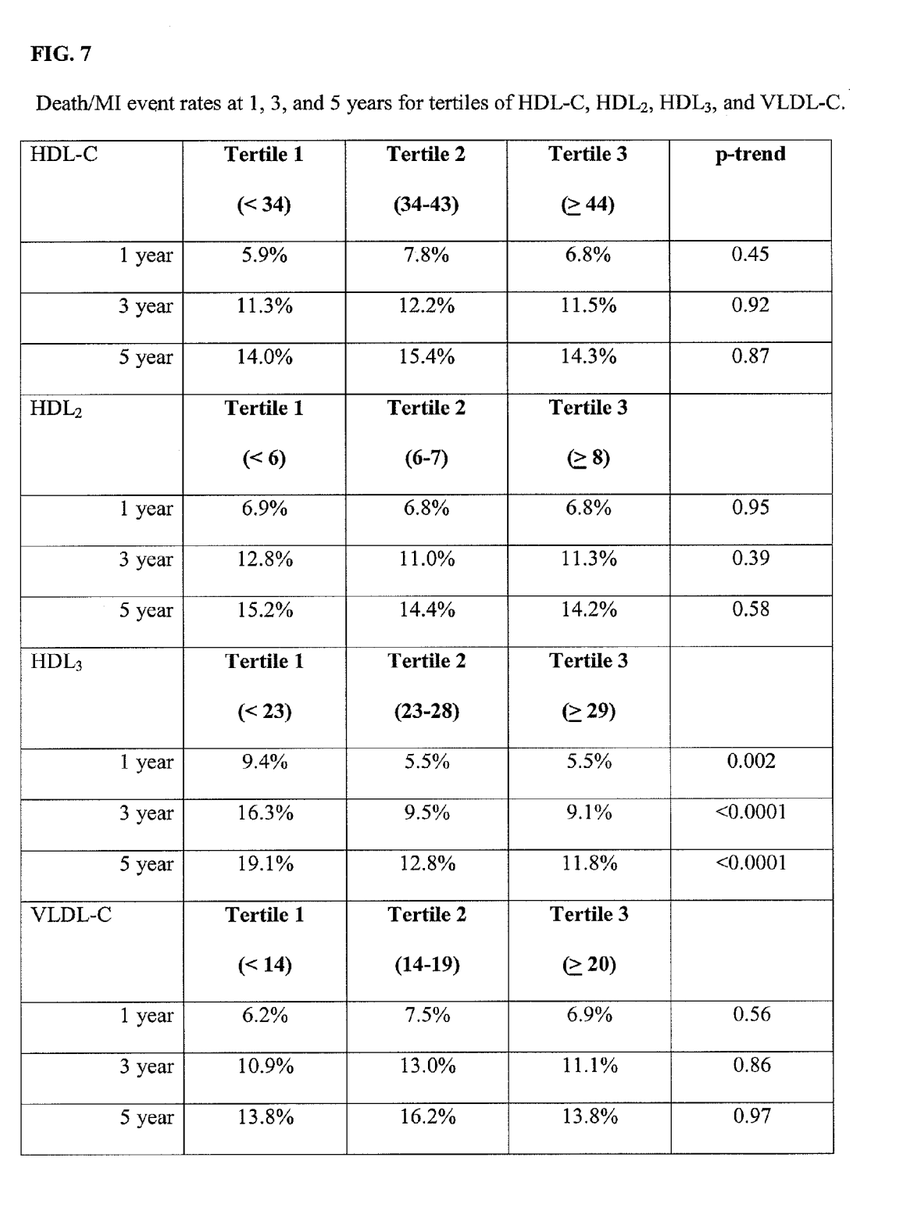
FIG. 7 shows death/MI event rates at 1, 3, and 5 years for tertiles of HDL-C, $HDL_2$-C, $HDL_3$-C, and VLDL-C.

Predictive Ability of the Individual Lipoprotein Subfractions Used to Estimate VAP Apolipoprotein A1 Levels In order to better understand the contribution to risk for D/MI of the lipoproteins used in this study to estimate Apo A1 levels (i.e. $HDL_2$-C, $HDL_3$-C, and VLDL-C) by the VAP method, we assessed the individual predictive value of these lipoproteins. FIG. 7 shows D/MI event rates at 1, 3, and 5 years for tertiles of HDL-C, $HDL_2$-C (T1: <6 mg/dL, T2: 6-7 mg/dL, T3: ≥8 mg/dL), $HDL_3$-C (T1: <23 mg/dL, T2: 23-28 mg/dL, T3: ≥29 mg/dl), and VLDL-C (T1: <14 mg/dL, T2:

14-19 mg/dL, T3: ≥20 mg/dL). Only $HDL_3$-C was associated with D/MI at all time points. D/MI rates were significantly lower for tertile 3, which has highest $HDL_3$-C levels, compared to T1 which has the lowest $HDL_3$-C concentration. Multivariable associations of $HDL_3$-C with D/MI were: 1-year: continuous: HR=0.97, p=0.02; T2 vs T1: HR=1.05, p=0.85; T3 vs T1: HR=0.62, p=0.03; 3-year: continuous: HR=0.96, p<0.0001; T2 vs T1: HR=0.98, p=0.93; T3 vs T1: HR=0.54, p<0.0001; and 5-year: HR=0.96, p<0.0001; T2 vs T1: HR=0.96, p=0.79; T3 vs T1: HR=0.60, p<0.0001. Total HDL-C, $HDL_2$-C, and VLDL-C were not longitudinally associated with D/MI.

Furthermore, we evaluated 1, 3, and 5 year D/MI rates for $HDL_2$-C and $HDL_3$-C for patients based on HDL-C stratification (i.e., HDL-C≥40 mg/dL and HDL-C<40 mg/dL) similar to the results in FIG. 5. It was found that $HDL_3$-C, but not $HDL_2$-C (data not shown), was associated with D/MI in patients with HDL-C≥40 mg/dL, but not in patients with HDL-C<40 mg/dL. For patients with an HDL-C mg/dL, $HDL_3$-C T1 had a D/MI rate of 13.8% at year 1 compared to 6.5% and 4.9%, respectively, for T2 and T3 (p-trend<0.0001). The corresponding results for years 3 and 5 were also highly significant (p-trend<0.0001 for year 3 and p-trend=0.001 for year 5). When longitudinal associations were evaluated for $HDL_2$-C and $HDL_3$-C stratified by HDL-C values (≥40 mg/dL and <40 mg/dL), $HDL_3$-C at all time points (continuous and T1 vs T3) were associated with D/MI for patients with HDL-C≥40 mg/dL, but not for patients with HDL-C<40 mg/dL (data not shown). $HDL_2$-C was not associated with D/MI for either group of patients. Furthermore, only $HDL_3$-C was inversely associated with angiographically determined CAD ($HDL_3$-C: T1=57.9%, T2=55.3%, T3=48.6%, p-trend<0.0001), but not $HDL_2$-C (T1=56.4%, T2=55.7%, T3=49.5%, p-trend=0.10). These results suggest that only $HDL_3$-C, but not $HDL_2$-C or total HDL-C is predictive of future D/MI.

Comparison with Immunoassay Measured Apo A1

Apo A1 results used in this study (VAP estimated apo A1) were derived using an equation which involved VAP measured cholesterol concentrations of $HDL_2$-C, $HDL_3$-C, and VLDL-C as described above. However, in order to verify the validity of the results obtained using apo A1 estimated by the VAP measurements, apo A1 was also directly measured in 1,478 of the 2,414 patients using an immunoassay method (Abbott/Architect C8000) whose calibrator value was assigned by the manufacturer using a reference method calibrated against WHO/IFCC/CDC apo A1 Reference Material SP1-01. The results obtained were compared with the corresponding VAP estimated apo A1 values from the same 1,478 patients. Apo A1 determined by the VAP method was found to be highly correlated with the apo A1 measured by Abbott immunoassay (r=0.854, p<0.0001). Mean immunoassay apo A1 levels were lower (106.8±22.9 mg/dL) and had a wider range of values (34.0-222.0 mg/dL) than VAP apo A1 levels (114.4±18.2 mg/dL; range: 69.3-200.3). Abbott apo A1 tertiles (T1: ≤96.0 mg/dL, T2: 96.1-113.0, and T3: >113.0) were slightly different than VAP apo A1 tertiles (FIG. 8).

Abbott apo A1 tertiles were significantly associated with CAD in a stepwise manner: T1=64.2%, T2=58.0%, T3=46.1%, p-trend<0.0001; as were VAP apo A1 tertiles (T1=64.6%, T2=57.4%, T3=46.5%, p-trend<0.0001). In determining D/MI risk, tertiles of Abbott apo A1 did not stratify risk as well as the VAP apo A1 tertiles (FIG. 8). D/MI at 3 years (p-trend=0.04) and 5 years (p-trend=0.005) had a significant inverse graded association with Abbott apo A1 tertiles, but not with 1 year (p-trend=0.10) D/MI. Multivariable associations were attenuated with Abbott apo A1 tertiles.

Figure 8:
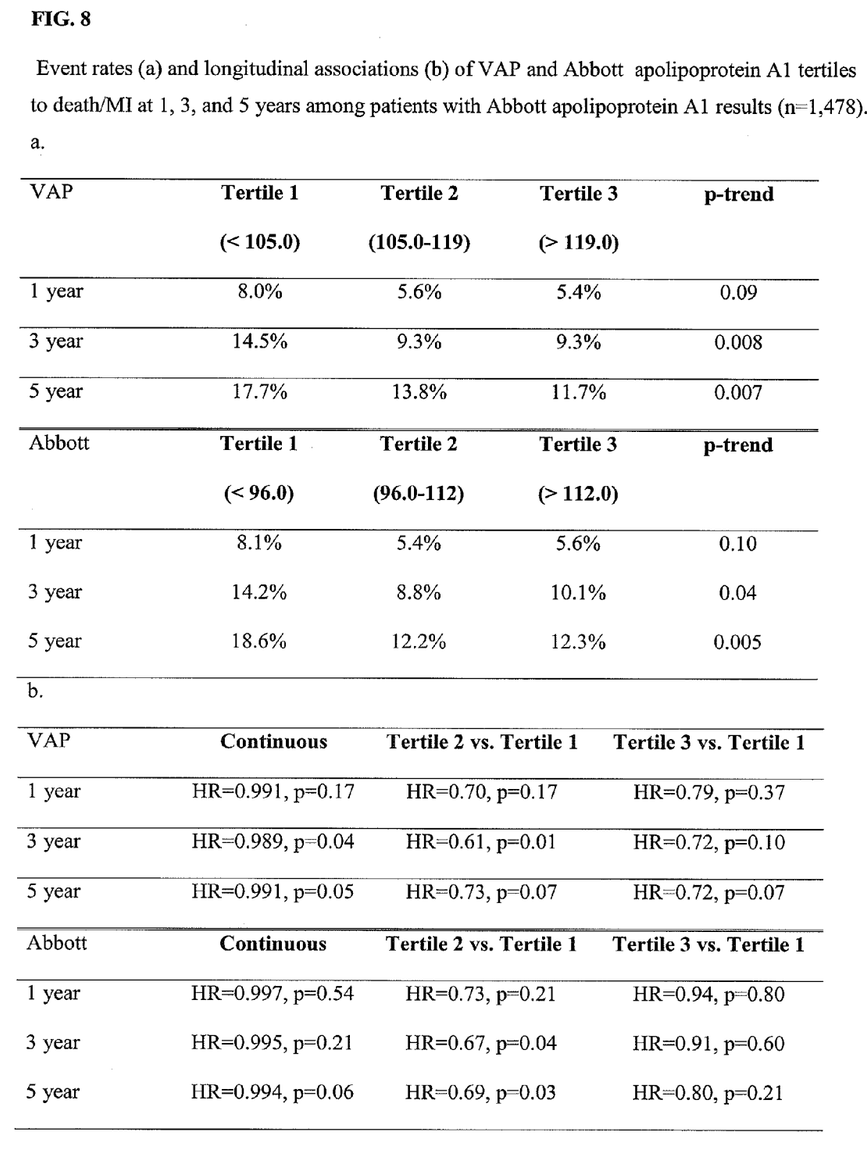
FIG. 8 shows event rates (a) and longitudinal associations (b) of VAP and Abbott apolipoprotein A1 tertiles to death/MI at 1, 3, and 5 years among patients with Abbott apolipoprotein A1 results (n=1,478).

The results in FIG. 8 show that VAP apo. A1 is a superior predictor of D/MI compared to immunoassay measured Abbott apo A1.

The invention claimed is:

1. A method of measuring a risk of coronary heart disease or a clinical manifestation of coronary heart disease in a subject known to have an HDL-C concentration of greater than or equal to 40 mg/dL, the method consisting essentially of: determining the concentration of apo A1 in the subject's serum; and determining the presence of an elevated risk if the concentration of apo A1 is below a threshold concentration, wherein the apo A1 concentration is determined by applying the following equation: $[(2.4591*HDL_3\text{-}C)+(0.611*HDL_2\text{-}C)+(0.555*VLDL\text{-}C)+33.75]$.

2. The method of claim 1, wherein the determining step is performed ex vivo.

3. The method of claim 1, wherein the threshold concentration is 118 mg dL and the subject is male.

4. The method of claim 1, wherein the threshold concentration is 145 mg/dL and the subject is female.

5. The method of claim 1, wherein the apo A1 concentration is measured without measuring apo B.

6. The method of claim 1 where the coronary heart disease or clinical manifestation of coronary heart disease is a risk of death or myocardial infarction.

7. A method of measuring a risk of death or myocardial infarction in a subject known to have an HDL-C concentration of greater than or equal to 40 mg/dL, the method consisting essentially of determining the concentration of apo A1 in the subject's serum; and determining the presence of an elevated risk if the concentration of apo A1 is below a threshold concentration, wherein the apo A1 concentration is determined by applying the following equation: $[(2.4591*HDL_3\text{-}C)+(0.611*HDL_2\text{-}C)+(0.555*VLDL\text{-}C)+33.75]$.

8. The method of claim 7, wherein the determining step is performed ex vivo.

9. The method of claim 7, wherein the apo A1 concentration is measured without measuring apo B.

10. The method of claim 7, wherein the threshold concentration is 118 mg dL and the subject is male.

11. The method of claim 7, wherein the threshold concentration is 145 mg/dL and the subject is female.

12. A method of measuring a risk of coronary heart disease or a clinical manifestation of coronary heart disease in a subject the method consisting essentially of determining the concentration of both apo A1 and HDL-C in the subject's serum; and determining the presence of an elevated risk if the concentration of apo A1 is below a threshold concentration and the HDL-C concentration is greater than or equal to 40 mg/dl, wherein the apo A1 concentration is determined by applying the following equation: $[(2.4591*HDL_3\text{-}C)+(0.611*HDL_2\text{-}C)+(0.555*VLDL\text{-}C)+33.75]$.

13. The method of claim 12, wherein the determining step is performed ex vivo.

14. The method of claim 12, wherein the HDL-C concentration is determined directly.

15. The method of claim 12, wherein the apo A1 concentration is measured without measuring apo B.

16. The method of claim 12 where the coronary heart disease or clinical manifestation of coronary heart disease is a risk of death or myocardial infarction.

17. The method of claim 12, wherein the threshold concentration is 118 mg dL and the subject is male.

18. The method of claim 12, wherein the threshold concentration is 145 mg/dL and the subject is female.

* * * * *